United States Patent [19]

Legoux et al.

[11] Patent Number: 5,279,947
[45] Date of Patent: Jan. 18, 1994

[54] DNA SEQUENCE PARTICIPATING IN THE REGULATION OF THE EXPRESSION OF A DNA SEQUENCE CODING FOR A PRECURSOR OF A POLYPEPTIDE, EXPRESSION VECTORS AND PROCESS FOR THE PERIPLASMIC PRODUCTION OF THE POLYPEPTIDE

[75] Inventors: Richard Legoux, Caraman; Pascal Leplatois, Cuo Toulza; Evelyne Joseph-Liauzun, Saint Orens De Gameville, all of France

[73] Assignee: Sanofi, Paris, France

[21] Appl. No.: 931,495

[22] Filed: Aug. 21, 1992

Related U.S. Application Data

[63] Continuation of Ser. No. 397,787, Aug. 24, 1989, abandoned.

[30] Foreign Application Priority Data

Aug. 24, 1988 [FR] France .................. 88 11187

[51] Int. Cl.$^5$ .............. C12N 15/00; C12N 15/18; C12N 1/21
[52] U.S. Cl. .................. 435/69.1; 435/69.4; 435/172.3; 435/252.33; 435/320.1; 536/23.5; 536/23.51
[58] Field of Search ............ 536/27, 23.5, 23.51; 435/69.1, 69.4, 252.33, 172.3, 320.1

[56] References Cited

U.S. PATENT DOCUMENTS 4,945,047 7/1990 Legoux et al. .................. 435/69.4

FOREIGN PATENT DOCUMENTS 0241446 3/1987 European Pat. Off. .
0245217 4/1987 European Pat. Off. .
0251842 6/1987 European Pat. Off. .
2597114 4/1986 France .

OTHER PUBLICATIONS

Pharmacia Molecular Biologicals Catalog, May 1986, pp. 96-99, Uppsala, Sweden ("Chemicals and equipment for molecular biology," pp. 96 and 99)
Shinozaki, K. et al., *Gene*, 24: 147-155, 1983.
Brosius, et al.; Gene Organization and Primary Structure of a Ribosomal RNA Operon from *Escherichia coli*; J. Mol. Biol. (1981); 148: 107-127.

*Primary Examiner*—Robert J. Hill, Jr.
*Assistant Examiner*—Marianne Porta Allen
*Attorney, Agent, or Firm*—Foley & Lardner

[57] ABSTRACT

DNA sequence participating in the regulation of the expression of a DNA sequence coding for a precursor of a polypeptide.

Expression vectors containing such a sequence.

Process for the periplasmic production of a polypeptide in a strain of Gram-negative bacteria transformed by one of these vectors.

Application to the production of human growth hormone.

10 Claims, 3 Drawing Sheets

DNA SEQUENCE PARTICIPATING IN THE REGULATION OF THE EXPRESSION OF A DNA SEQUENCE CODING FOR A PRECURSOR OF A POLYPEPTIDE, EXPRESSION VECTORS AND PROCESS FOR THE PERIPLASMIC PRODUCTION OF THE POLYPEPTIDE

This application is a continuation, of application Ser. No. 07/397,787, filed Aug. 24, 1989, now abandoned.

The invention relates to a DNA sequence participating in the regulation of the expression of a DNA sequence coding for a precursor of a polypeptide. It further relates to the expression vectors into which such a sequence is introduced. It further relates to the process which consists in expressing these vectors in a strain of Gram-negative bacteria for the periplasmic production of a polypeptide. It relates more particularly to a process for the production of human growth hormone.

It is known that Gram-negative bacteria, and more particularly strains of the species *Escherichia coli*, are preferred hosts for the production of heterologous polypeptides, i.e. polypeptides which are not normally synthesized by the strain used, and especially polypeptides of eukaryotic origin. They are suitable for the production of polypeptides synthesized in the form of a prepolypeptide called a precursor. In fact, only the mature form passes through the cell membrane and accumulates in the periplasm, from which it can be extracted simply by an osmotic shock. The purification of the polypeptide obtained in this way is simplified because it is a major component of the periplasm.

The advantages of such a production are rendered all the more appreciable the greater the efficiency of the transcription of the DNA sequence coding for said precursor, the translation of the messenger RNA and then the passage of the mature polypeptide through the cell membrane.

Ways of improving the transcription have been widely studied. Improvement involves designing high-strength promoter sequences which are easy to control. European patent applications A-067540 and A-018069 relate to the protection of such sequences.

A few studies have been devoted to ways of improving the translation. Thus European patent application A-0 241 446 has disclosed novel DNA sequences located upstream from the Shine-Dalgarno sequence, the transcription of which yields a sequence of the messenger RNA hybridizing specifically with nucleotides 447 to 487 of ribosomal RNA 16S (or rRNA 16S), which is an essential constituent of the ribosomes. The resulting modification of the ribosome binding site is said to make the translation more efficient for heterologous proteins synthesized in the form of an N-methionylated mature protein accumulating in the bacterial cytoplasm.

The applicant checked whether one of the preferred constructions described in European patent application A-0 241 446 would be suitable for the production of polypeptides localized in the periplasm. For lack of a satisfactory result, it attempted to introduce, up-stream from the Shine-Dalgarno sequence, other DNA sequences whose transcription would yield a messenger RNA sequence capable of hybridizing with rRNA 16S. There proved to be a large number of such sequences, but few of them had the expected efficacy. On the other hand, this research led the applicant to identify a sequence of great interest.

According to a first aspect, the invention relates precisely to a DNA sequence participating in the regulation of the expression of a DNA sequence coding for a precursor of a polypeptide, which regulatory DNA sequence contains n nucleotides, n being between 4 and 10, at least n-1 of these nucleotides being complementary to nucleotides 970 to 978 of rRNA 16S.

The ribosomal RNA 16S sequence in question has formula (a):

| 3' AAGAAGCGC 5' |
|---|
| in which |
| A = Adenosine monophosphate |
| C = Cytidine monophosphate |
| G = Guanosine monophosphate |

The regulatory sequence according to the invention advantageously has formula (b):

| 5' TTTTTCGCG 3' |
|---|
| in which |
| A = Thymidine monophosphate |
| C = Cytidine monophosphate |
| G = Guanosine monophosphate |

Sequence (b) is complementary to sequence (a) for 8 of its 9 nucleotides; its transcription determines, on the corresponding messenger RNA, a sequence 5' UUUU-UCGCG 3' (U=Uracil) which is complementary for 8 of its 9 nucleotides to the ribosomal RNA 16S sequence between nucleotides 970 and 980, 5' CGCGAAGAA 3'. The efficacy of this regulatory sequence (b) is all the more unexpected because it is known that nucleotides 972 to 975, CGAA, of ribosomal RNA 16S are normally involved in a bond with nucleotides 960 to 963, UUCG, of said RNA so as to contribute to the stabilization of its secondary structure (H. F. NOLLER, Science, 212 (1981) 403–411).

The invention is not limited to this particular DNA sequence TTTTTCGCG. It further relates to any sequence of the type TTXTTCGCG, in which X=A, C or G, and any sequence which is derived from the latter and contains a series of at least 4 of its nucleotides, on condition that, in the corresponding messenger RNA sequence, 4 of the nucleotides hybridize with nucleotides 970 to 978 of rRNA 16S.

The sequence according to the invention is located upstream from the Shine-Dalgarno sequence stricto sensu. It must not be more than 10 nucleotides away from it. Preferably, it is separated from it by only 4 nucleotides.

The other regulatory sequences located on either side of the sequence according to the invention can take the known forms. In particular, the nature of the promoter is of little importance.

According to another aspect, the invention relates to the expression vectors into which a sequence coding for a precursor of a polypeptide, and located downstream from and under the control of a regulatory sequence containing a sequence according to the invention, has been inserted.

These expression vectors can be of any kind and are preferably plasmids.

According to another aspect, the invention relates to a process for the periplasmic production of a polypeptide. A characteristic feature of this process, which consists in transforming a strain of Gram-negative bacteria with an expression vector carrying a sequence coding for a precursor of a polypeptide, and in cultivating the transformed bacteria so as to permit the expression of this sequence and the maturation of the precursor by passage through the cytoplasmic membrane of the mature polypeptide accumulating in the periplasm, is the use of a vector carrying a sequence according to the invention.

The nature of the bacterial strain is of little importance. It appears in particular that strains carrying a mutation affecting at least one or other of the cya and crp genes, such as the strains described in European patent application A-0245138, are suitable.

The process according to the invention is appropriate for the production of polypeptides synthesized in the form of a precursor. The sequence coding for the precursor can correspond either to a natural sequence or to a sequence which has been wholly or partially modified as regards its part coding for the signal peptide. It can also be a hybrid sequence in which a sequence coding for a natural or unnatural signal peptide is associated with a sequence coding for the mature polypeptide.

The process according to the invention is particularly appropriate for the production of polypeptides which are heterologous relative to the strain used, especially polypeptides of eukaryotic origin.

In one embodiment, the invention relates precisely to a process for the production of human growth hormone (or hGH).

The present invention will now be described in greater detail with the aid of the following example in which reference will be made to the three Figures attached.

- = Localization of the origin of replication (ORI).
- = DNA segment derived from plasmid pBR322.
- = DNA segment containing the sequence coding for a natural precursor of hGH.
- = DNA segment of phage fd containing a transcription terminator.
- = DNA segment containing a UV5 tryptophan-lactose hybrid promoter-operator.
- = DNA segment coding for β-lactamase (ApR: ampicillin resistance).

Figure 2:
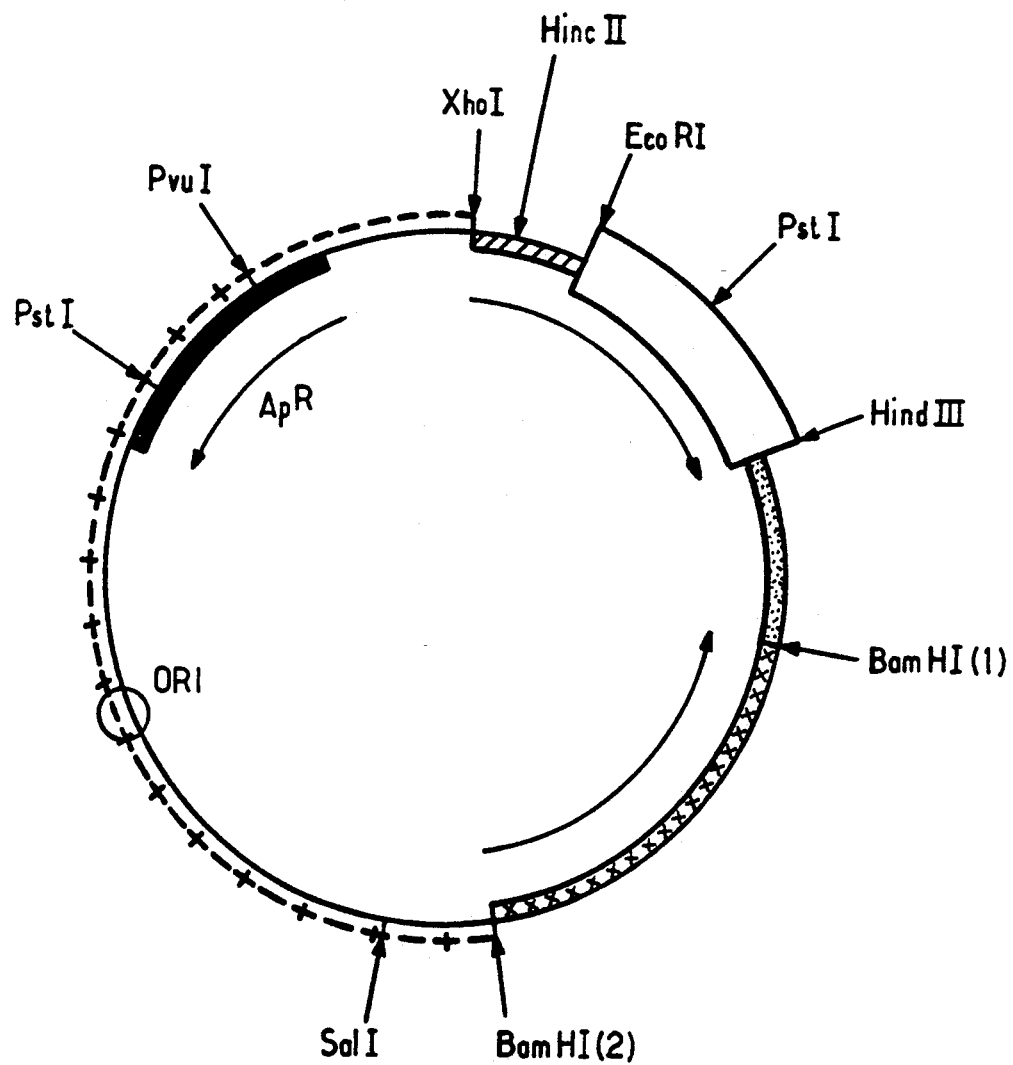

FIG. 2 shows the restriction map of a plasmid whose PvuI-XhoI-BamHI(1) and PvuI-ORI-BamHI(2) fragments originate from plasmids p163,1 and pBR327 respectively and whose small BamHI(2)-BamHI(1) fragment is fragment 3 described in Example 1 below.

Figure 3:
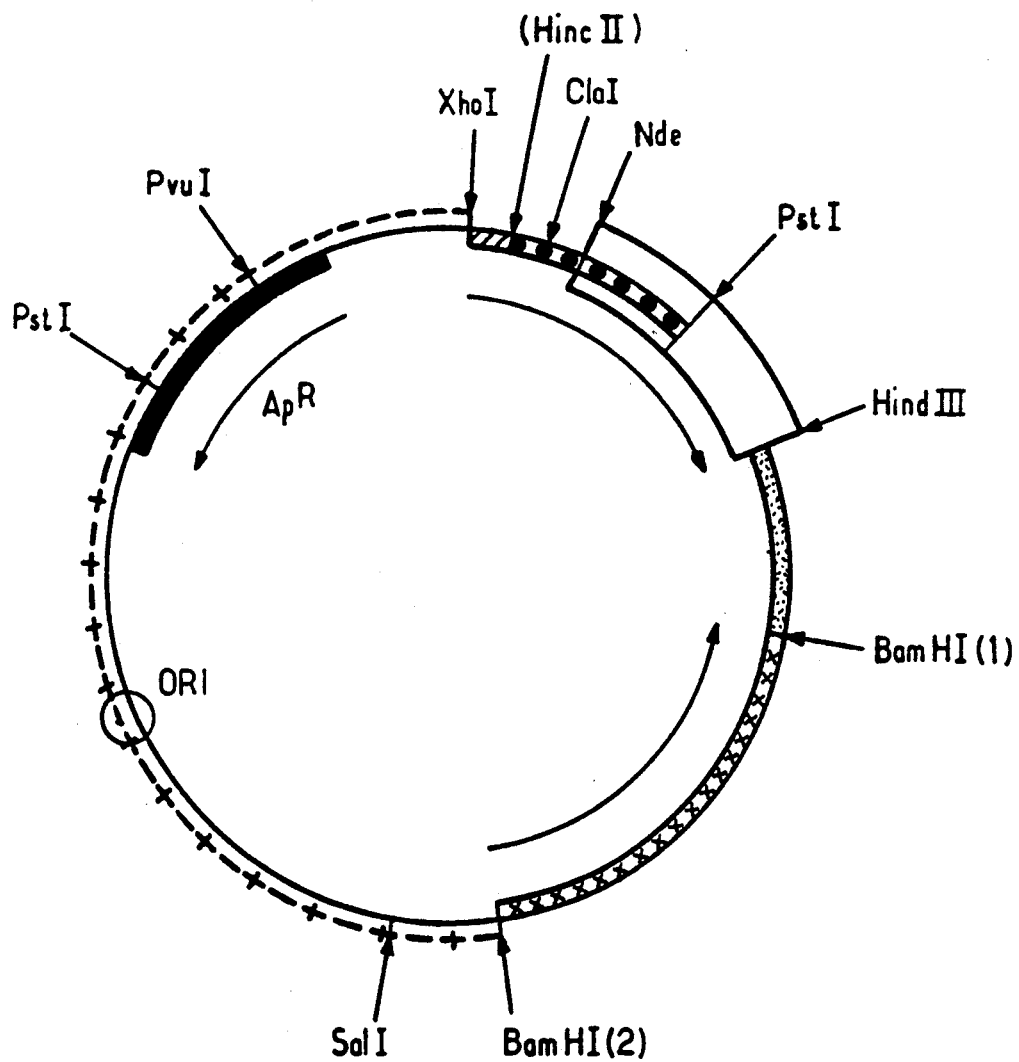

FIG. 3 shows a restriction map common to plasmids p380,1 and p373,2. The different restriction segments are labeled arbitrarily according to the following legend:

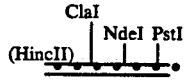

- −+−+−+− = PvuI-BamHI sequence derived from plasmid pBR327.
- ------------ = PvuI-XhoI sequence derived from plasmid p163,1.
- ▨▨▨▨▨ = XhoI-HincII sequence derived from plasmid p163,1.
- (HincII) ClaI | NdeI PstI = Fragment 4 described in Example 1 below.
- XXXXXXXX = Fragment 3 described in Example 1 below.
- ⋮⋮⋮⋮⋮⋮⋮ = DNA fragment of phage fd containing a transcription terminator.

EXAMPLE

Periplasmic production of human growth hormone

1. Bacteria and plasmids used

One bacterial strain and four plasmids were used.

The strain used is a strain of the species *Escherichia coli* which is directly related to the strain described in European patent application A-0245138, deposited in the Collection Nationale de Cultures de Microorganismes (CNCM, Paris, France) on Feb. 17, 1986 under the reference I-529. This strain carries a cya mutation by deletion and a crp mutation by deletion.

The plasmids are those referred to below as p380,1, p381,1, p373,2 and p371,1.

Construction of the plasmids

The strategy employed utilized fragments obtained from already existing plasmids available to the public and fragments prepared by synthesis according to the techniques now in common use.

Figure 1:
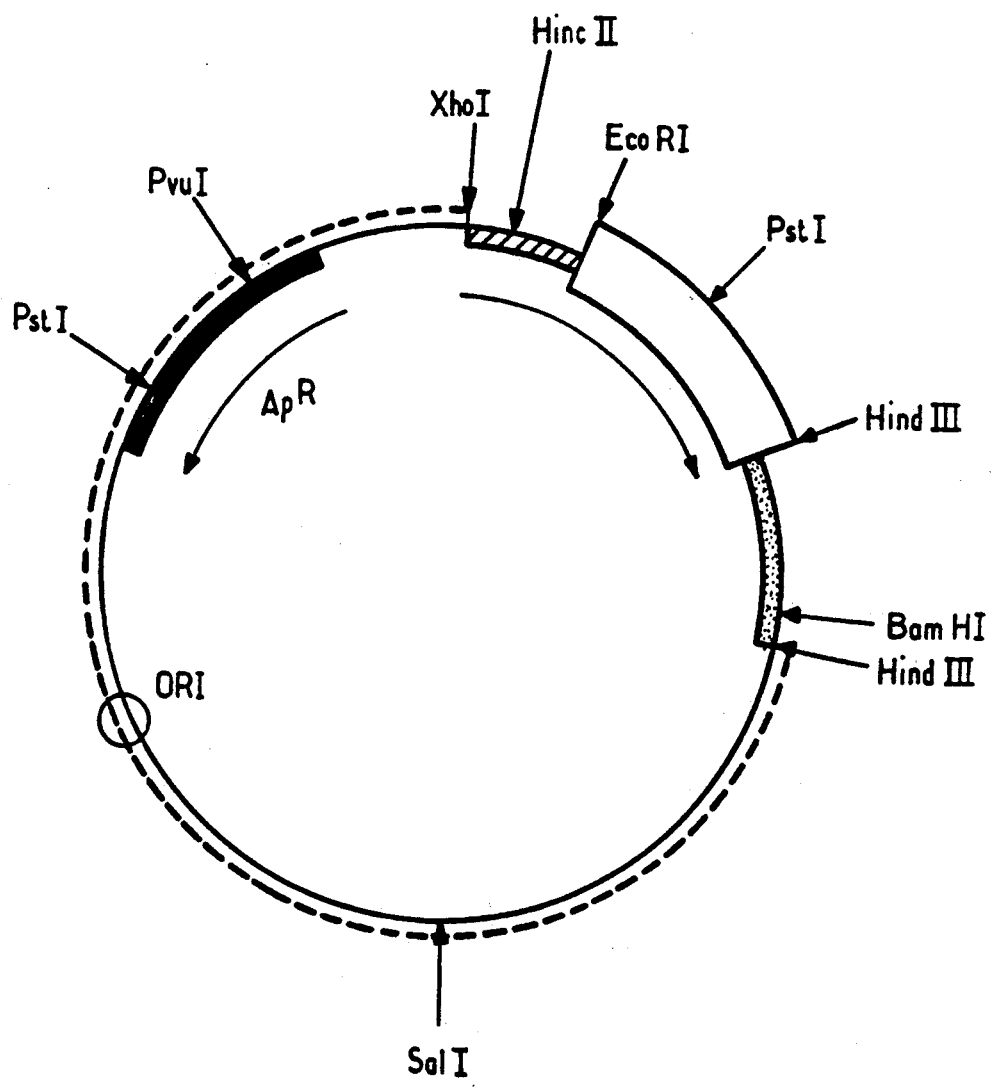
FIG. 1 shows a restriction map of plasmid p163,1. The different restriction segments are labeled arbitrarily according to the following legend.

Plasmid p163,1 (FIG. 1), described in European patent application A-0245138 and deposited in the CNCM under the reference I-530 on Feb. 17, 1986, was digested with the enzymes PvuI and BamHI. The PvuI-BamHI fragment—hereafter fragment 1-containing the action site of the restriction enzyme XhoI, shown in FIG. 1, was purified.

Likewise, plasmid pBR327, well known to those skilled in the art (q.v. SOBERON, X. et al., Gene, 9 (1980) 287-305), was digested with the enzymes PvuI and BamHI. The PvuI-BamHI fragment—hereafter fragment 2-containing the origin of replication, was purified.

Fragment 3 was then prepared; this is a synthetic BamHI(1)-BamHI(2) fragment containing the lac i gene and its promoter and having the following DNA sequence, on which the 2 ends of the strand are identified by the numbers 1 and 2 in order to specify the orientation of the fragment in the plasmids described in FIGS. 2 and 3:

FRAGMENT 3

BamHI(1)

-continued

| 5' GATCC | GCGGAAGCAT | AAAGTGTAAA | GCCTGGGGTG | CCTAATGAGT |
|---|---|---|---|---|
| GAGCTAACTT | ACATTAATTG | CGTTGCGCTC | ACTGCCCGCT | TTCCAGTCGG |
| GAAACCTGTC | GTGCCAGCTG | CATTAATGAA | TCGGCCAACG | CGCGGGGAGA |
| GGCGGTTTGC | GTATTGGGCG | CCAGGGTGGT | TTTTCTTTTC | ACCAGTGAGA |
| CGGGCAACAG | CTGATTGCCC | TTCACCGCCT | GGCCCTGAGA | GAGTTGCAGC |
| AAGCGGTCCA | CGCTGGTTTG | CCCCACCACC | CGAAAATCCT | GTTTGATGGT |
| GGTTAACGGC | GGGATATAAC | ATGAGCTGTC | TTCGGTATCG | TCGTATCCCA |
| CTACCGAGAT | ATCCGCACCA | ACGCGCAGCC | CGGACTCGGT | AATGGCGCGC |
| ATTGCGCCCA | GCGCCATCTG | ATCGTTGGCA | ACCAGCATCG | CAGTGGGAAC |
| GATGCCCTCA | TTCAGCATTT | GCATGGTTTG | TTGAAAACCG | GACATGGCAC |
| TCCAGTCGCC | TTCCCGTTCC | GCTATCGGCT | GAATTTGATT | GCGAGTGAGA |
| TATTTATGCC | AGCCAGCCAG | ACGCAGACGC | GCCGAGACAG | AACTTAATGG |
| GCCCGCTAAC | AGCGCGATTT | GCTGGTGACC | CAATGCGACC | AGATGCTCCA |
| CGCCCAGTCG | CGTACCGTCT | TCATGGGAGA | AAATAATACT | GTTGATGGGT |
| GTCTGGTCAG | AGACATCAAG | AAATAACGCC | GGAACATTAG | TGCAGGCAGC |
| TTCCACAGCA | ATGGCATCCT | GGTCATCCAG | CGGATAGTTA | ATGATCAGCC |
| CACTGACGCG | TTGCGCGAGA | AGATTGTGCA | CCGCCGCTTT | ACAGGCTTCG |
| ACGCCGCTTC | GTTCTACCAT | CGACACCACC | ACGCTGGCAC | CCAGTTGATC |
| GGCGCGAGAT | TTAATCGCCG | CGACAATTTG | CGACGGCGCG | TGCAGGGCCA |
| GACTGGAGGT | GGCAACGCCA | ATCAGCAACG | ACTGTTTGCC | CGCCAGTTGT |
| TGTGCCACGC | GGTTGGGAAT | GTAATTCAGC | TCCGCCATCG | CCGCTTCCAC |
| TTTTTCCCGC | GTTTTCGCAG | AAACGTGGCT | GGCCTGGTTC | ACCACGCGGG |
| AAACGGTCTG | ATAACAGACA | CCGGCATACT | CTGCGACATC | GTATAACGTT |
| ACTGGTTTCA | CATTCACCAC | CCTGAATTGA | CTCTCTTCCG | GGCGCTATCA |
| TGCCATACCG | CGAAAGGTTT | TGCGCCATTC | GATGGTGTCC | G 3' |
| | | | | BamHI(2) |

Fragments 1, 2 and 3 were then ligated to give the intermediate plasmid described in FIG. 2.

This plasmid was subjected to partial digestion with the restriction enzymes HincII and PstI. The HincII-PstI fragment, containing the origin of replication and shown in FIG. 3, was then ligated to fragment 4 shown below, which is a synthetic DNA fragment carrying a sequence coding for the first 44 amino acids of a natural precursor of hGH and, upstream from this sequence, regulatory signals.

FRAGMENT 4

In this fragment, the amino acids are designated by letters according to the following code:

A = alanine
C = cysteine
D = aspartic acid
E = glutamic acid
F = phenylalanine
G = glycine
H = histidine
I = isoleucine

```
                                                              ClaI
5' TCGAGCTGACTGACCTGTTGCTTATATTACATCGA
   AGCTCGACTGACTGGACAACGAATATAATGTAGCT
                                                              NdeI

NdeI
TAGCGTATAATGTGTGGAATTGTGAGCGGATAACAATTTCACACAGXXXXXXXXXXAAGAAGGAGATATACAT
ATCGCATATTACACACCTTAACACTCGCCTATTGTTAAAGTGTGTCXXXXXXXXXXTTCTTCCTCTATATGTA

ATG GCT ACC GGA TCC CGG ACT AGT CTG CTC CTG GCT TTT GGC CTG CTC TGC CTG
TAC CGA TGG CCT AGG GCC TGA TCA GAC GAG GAC CGA AAA CCG GAC GAC ACG GAC
 M   A   T   G   S   R   T   S   L   L   L   A   F   G   L   L   C   L
-26

XbaI
CCC TGG CTT CAA GAG GGC AGT GCC TTC CCA ACC ATT CCC TTA TCT AGA CTT TTT
GGG ACC GAA GTT CTC CCG TCA CGG AAG GGT TGG TAA GGG AAT AGA TCT GAA AAA
 P   W   L   Q   E   G   S   A   F   P   T   I   P   L   S   R   L   F
                        -1   1

GAC AAC GCT ATG CTC CGC GCC CAT CGT CTG CAC CAG CTG GCC TTT GAC ACC TAC
CTG TTG CGA TAC GAG GCG CGG GTA GCA GAC GTG GTC GAC CGG AAA CTG TGG ATG
 D   N   A   M   L   R   A   H   R   L   H   Q   L   A   F   L   T   Y

PstI
CAG GAG TTT GAA GAA GCC TAT ATC CCA AAG GAA CAG AAG TAT TCA TTC CTG CA
GTC CTC AAA CTT CTT CGG ATA TAG GGT TTC CTT GTC TTC ATA AGT AAG G      5'
 Q   E   F   E   E   A   Y   I   P   K   E   Q   K   Y   S   F
                                                              44
```

-continued

K = lysine
L = leucine
M = methionine
N = asparagine
P = proline
Q = glutamine
R = arginine
S = serine
T = threonine
V = valine
W = trytophan
Y = tyrosine Sequences -35 (TTGCTT) and -10 (TATAAT) of the promoter sequence, and the Shine-Dalgarno sequence well known to those skilled in the art, are underlined in that order. The symbols X positioned upstream from this sequence represent the following particular series of 9 nucleotides:

| 5' | TTTAACTTT | |
|----|-----------|----|
|    | AAATTGAAA | 5' |

Plasmid p380,1 was obtained in this way.

Plasmid p380,1 (FIG. 3) was used to construct 3 other plasmids by replacing its ClaI-NdeI fragment, marked on fragment 4 above, with each of the following 3 ClaI-NdeI fragments:

Fragment a
ClaI
5' CGATAGCGTATAATGTGTGGAATTGTGAGCGGATAACA
    TATCGCATATTACACACCTTAACACTCGCCTATTGT NdeI
ATTTCACACAGTCTCCCCGCAAGAAGGAGATATACA
TAAAGTGTGTCAGAGGGGCGTTCTTCCTCTATATGTAT 5'

Fragment b
ClaI
5' CGATAGCGTATAATGTGTGGAATTGTGAGCGGATAACA
    TATCGCATATTACACACCTTAACACTCGCCTATTGT NdeI
ATTTCACACAGTCAATGAGCAAGAAGGAGATATACA
TAAAGTGTGTCAGTTACTCGTTCTTCCTCTATATGTAT 5'

Fragment c
ClaI
5' CGATAGCGTATAATGTGTGGAATTGTGAGCGGATAACA
    TATCGCATATTACACACCTTAACACTCGCCTATTGT NdeI
ATTTCACACAGTTTTTCGCGAAGAAGGAGATATACA
TAAAGTGTGTCAAAAAGCGCTTCTTCCTCTATATGTAT 5'

The plasmids obtained are plasmid p381,1 with fragment a, plasmid p371,1 with fragment b and plasmid p373,2 with fragment c.

2. General methodology

The experiments performed consisted in cultivating the host-vector systems in question, prepared beforehand (cf. ¶ 2.1), under conditions such as to give an adequate biomass (cf. ¶ 2.2) and such that the cells subjected to induction produce hGH (cf. ¶ 2.3), in collecting the proteins contained in the periplasmic space by osmotic shock (cf. ¶ 2.4) and in determining the periplasmic hGH (cf. ¶ 2.5).

2.1 Preparation of the host-vector systems

The host-vector systems were prepared according to the bacterial transformation techniques known to those skilled in the art, which are described especially in the following books:

Molecular cloning—A Laboratory Manual—T. Maniatis, E. F. Fritsch and J. Sambrook—Cold Spring Harbor Laboratory—1982.

Experiments in Molecular Genetics—J. H. MILLER—Cold Spring Harbor Laboratory—1972.

2.2 Culture a) Inoculation

An isolated colony obtained on a solid medium (LB medium+agar-agar) was suspended in 5 ml of a medium (LB medium).

The LB medium used has the following characteristics:

its components introduced before autoclaving are:

| Bactotryptone   | 10 g   |
|-----------------|--------|
| yeast extract   | 5 g    |
| sodium chloride | 5 g    |
| distilled water | qs 1 l | its pH is adjusted to 7.3 before autoclaving;
ampicillin is added after autoclaving at a rate of 100 µg/ml.

b) Incubation

The suspension prepared in a was incubated at 37° C. for 18 h in order to allow the culture to reach the stationary growth phase. The dense suspension obtained was diluted in LB medium to give an optical density value close to 0.03 when read at 600 nm—OD at 600 nm—and 25 ml of this bacterial suspension were then incubated at 37° C., with agitation, until the OD at 600 nm was of the order of 0.3.

2.3 Induction

Isopropyl-β-D-thiogalactose (or IPTG) was added to the bacterial suspension obtained according to 2.2.b in an amount such that its final concentration was equal to 1 mM; IPTG was used here to initiate and maintain the synthesis of the precursor of hGH by neutralizing the action of the repressor which normally binds to the lactose operator.

The suspension, with IPTG added, was agitated at 37° C. for 2 h 30 min.

2.4 Osmotic shock

Reference was made to the protocol described by N. G. NOSSAL and L. A. HEPPEL in "The Journal of Biological Chemistry, 241 (1966) 3055–3063".

a) Washing with tris and EDTA

A sample of the suspension as obtained in 2.3 after induction was taken and centrifuged for 5 minutes at 6000 g.

The residue was taken up in a volume of buffer at pH 7 (solution A) (cf. above) such that the suspension obtained had an OD at 600 nm of the order of 10.

The buffer used was prepared by adding the following to distilled water:
tri(hydroxymethyl)aminomethane-HCl, or tris-HCl, added so as to give a final concentration of 30 mM.
ethylenediaminetetraacetic acid, or EDTA, added so as to give a final concentration of 1 mM.

b) Action of sucrose

The suspension obtained in 2.4.a was centrifuged for 5 minutes at 6000 g.

The residue was taken up very carefully, at constant volume, in a solution B prepared for immediate use and corresponding to solution A to which sucrose has been added at a rate of 15 g per 100 ml.

The suspension was left for 10 minutes at 20° C.
It was then centrifuged for 5 minutes at 6000 g.
The centrifuge tubes were placed in melting ice.

The supernatant was carefully removed and replaced (at constant volume) with deionized water which had been cooled beforehand to the temperature of melting ice.

The suspension prepared in this way (having an OD at 600 nm of the order of 10) was left for 5 minutes at 0° C.

c) Collection of the proteins localized in the periplasm

The suspension obtained in 2.4.b was centrifuged for 10 minutes at 18,000 g.

The supernatant, which contained the proteins localized in the periplasm, was collected.

2.5 Determination of the periplasmic hGH

The supernatant obtained in 2.4.c was subjected to high pressure liquid chromatography using an apparatus equipped with a calibrated injection system and a detector set at 220 nm.

The following were used:
a C8—300 Angström reversed-phase column made of steel, with a length of 10 cm and an internal diameter of 4.6 mm (SYNCHROM reference C-8 R103-10),
a mobile phase consisting of a linear gradient passing from 70 volumes of solution S1 and 30 volumes of solution S2 to 40 volumes of solution S1 and 60 volumes of solution S2 in 20 minutes.

Solutions S1 and S2 has the following characteristics:
S1 = purified water containing 0.1% (v/v) of trifluoroacetic acid,
S2 = acetonitrile for HPLC, containing 0.08% (v/v) of trifluoroacetic acid,
the flow rate was 1 ml per minute.

The optical density of the fractions was measured and the amount of periplasmic hGH, expressed in micrograms per ml of supernatant, was determined by comparison with a previously established standard scale.

2.6 Analysis by the Western Blot technique

The following operations were carried out in succession:
separation by gel electrophoresis (according to the protocol described by LAEMMLI, U.K., Nature, 227 (1970) 680–685) of the different proteins contained in each of the supernatants obtained according to 2.4.c; the gel used was a polyacrylamide gel (15% w/v) containing 0.5% of sodium dodecylsulfate.
transfer of said proteins contained in the gel on to a nitrocellulose filter (according to the technique of H. TOWBIN et al., Proc. Natl. Acad. Sci. U.S.A., 76 (1979) 4350–4354).
immunodetection performed according to the technique of BURNETTE (W. W. BURNETTE, Anal. Biochem., 112 (1981) 195–203); this entails the following successive operations:
rinsing the nitrocellulose filter for 10 min with a buffer A (tris-HCl 10 mM, NaCl 170 mM, KI 1 mM),
bringing the nitrocellulose filter into contact with a buffer B (buffer A with bovine serum albumin added at a rate of 3 g per 100 ml) for 30 min at 37° C.,
bringing the nitrocellulose filter into contact with an immune serum (a polyclonal antibody recognizing mature hGH and its precursor) for 18 h at 20° C.,
rinsing the nitrocellulose filter with buffer B,
bringing the nitrocellulose filter into contact with a solution of protein A labeled with iodine 125 at a rate of 0.1 microcurie per ml, for 6 h at 20° C.,
rinsing the filter with buffer A,
drying the filter between two absorbent sheets,
bringing the filter into contact with an X-ray film,
developing the film.

3. Results

Presentation

It was noted that, under the chosen operating conditions, periplasmic hGH was present in its mature form for about 98% of the molecules, irrespective of the bacterial strain and the plasmid used.

The results of the determination are reported in the Table below:

| | | Plasmid tested | | | |
|---|---|---|---|---|---|
| | | 371,1 | 373,2 | 380,1 | 381,1 |
| 1 | OD at 600 nm, measured on the suspension obtained in 2.3 after induction | 1.38 | 1.32 | 0.30 | 1.38 |
| 2 | Periplasmic hGH | 0.73 | 2.13 | 3.56 | 0.24 |

|  | Plasmid tested | | | |
| --- | --- | --- | --- | --- |
|  | 371,1 | 373,2 | 380,1 | 381,1 |
| measured in micrograms per ml of supernatant collected after osmotic shock and brought to a turbidity such that OD at 600 nm = 1 | | | | |

Interpretation a) Row 1 reflects the growth rate of the bacterial cells. It is clearly apparent that plasmid 380,1 prohibits appropriate cell growth.

b) Row 2 reflects the capacity of each cell to produce periplasmic hGH. The result obtained with plasmid 380,1 cannot be taken into account in view of the conclusion noted above. It is clear that, of the other 3 plasmids, it is plasmid 373,2 which offers the best performance characteristics by affording a production almost 10 times and 3 times greater than that afforded by plasmids p381,1 and p371,1 respectively.

What is claimed is:

1. A recombinant DNA sequence comprising the following elements in the 5' to 3' direction, said elements being operatively linked:
   (i) a DNA sequence complementary to 16S ribosomal RNA of *Escherichia coli* and comprising the nucleotide sequence 5' TTXTTCGCG 3', wherein X is selected from the group consisting of A, C, G and T;
   (ii) a Shine-Dalgarno DNA sequence AGGA; and
   (iii) a DNA sequence encoding a precursor form of a polypeptide, wherein said precursor form consists of signal peptide operatively linked to a polypeptide, and wherein said precursor is converted in *Escherichia coli* to a mature form that lacks said signal peptide and localizes in the periplasm,
   wherein said DNA sequence of part (i) is not more than 10 nucleotides away from said Shine-Dalgarno DNA sequence AGGA.

2. A recombinant DNA sequence according to claim 1 wherein X=T in said DNA sequence complementary to 16S ribosomal RNA of *Escherichia coli*.

3. An expression vector comprising a recombinant DNA sequence according to claim 1.

4. An expression vector according to claim 3 which is a plasmid.

5. A strain of *Escherichia coli* transformed by an expression vector according to claim 3.

6. A strain of *Escherichia coli* according to claim 5, which comprises a deletion of the cya gene and a deletion of the crp gene.

7. A recombinant DNA sequence according to claim 6, wherein said DNA sequence complementary to 16S ribosomal RNA of *Escherichia coli* is located 4 nucleotides from said Shine-Dalgarno DNA sequence AGGA.

8. A recombinant DNA sequence according to claim 1, wherein said polypeptide is human growth hormone.

9. A process for periplasmic production of a polypeptide in *Escherichia coli* wherein said process comprises the following steps:
   (i) producing a transformed strain of *Escherichia coli*, wherein said transformed strain is transformed with an expression vector comprising a recombinant DNA sequence according to claim 1;
   (ii) incubating cells of said transformed strain under culture conditions that permit expression of said precursor form of said polypeptide followed by localization of the mature form of said polypeptide in the periplasm; and
   (iii) recovering said mature form of said polypeptide from said periplasm.

10. A process according to claim 9, wherein said recombinant DNA sequence of step (i) encodes a precursor form of human growth hormone.

* * * * *